(12) United States Patent
Nishizawa et al.

(10) Patent No.: US 9,011,886 B2
(45) Date of Patent: Apr. 21, 2015

(54) HAIR COSMETIC COMPOSITION

(75) Inventors: Eiichi Nishizawa, Cincinnati, OH (US); Akira Shiga, Sumida-ku (JP); Kenichi Ueyama, Sumida-ku (JP)

(73) Assignee: Kao Corporation, Tokyo (JP)

( * ) Notice: Subject to any disclaimer, the term of this patent is extended or adjusted under 35 U.S.C. 154(b) by 653 days.

(21) Appl. No.: 12/531,884

(22) PCT Filed: Apr. 17, 2008

(86) PCT No.: PCT/JP2008/001009
§ 371 (c)(1), (2), (4) Date: Sep. 18, 2009

(87) PCT Pub. No.: WO2008/132816
PCT Pub. Date: Nov. 6, 2008

(65) Prior Publication Data
US 2010/0104609 A1    Apr. 29, 2010

(30) Foreign Application Priority Data

Apr. 17, 2007  (JP) .................... 2007-108011
Dec. 14, 2007  (JP) .................... 2007-323008
Dec. 14, 2007  (JP) .................... 2007-323009

(51) Int. Cl.
| A61K 8/02 | (2006.01) |
| A61Q 5/12 | (2006.01) |
| A61K 8/73 | (2006.01) |
| A61K 8/891 | (2006.01) |
| A61K 8/03 | (2006.01) |
| A61K 8/892 | (2006.01) |
| A61Q 5/00 | (2006.01) |

(52) U.S. Cl.
CPC . *A61K 8/891* (2013.01); *A61K 8/03* (2013.01); *A61K 8/73* (2013.01); *A61K 8/892* (2013.01); *A61K 2800/594* (2013.01); *A61Q 5/00* (2013.01); *A61Q 5/12* (2013.01)

(58) Field of Classification Search
USPC ............................. 401/401, 70.12
See application file for complete search history.

(56) References Cited

U.S. PATENT DOCUMENTS

| 4,452,261 | A | * | 6/1984 | Bresak et al. ............ 132/206 |
| 5,620,681 | A | * | 4/1997 | Takata et al. ............ 424/59 |
| 5,660,190 | A | * | 8/1997 | Tricaud et al. ........... 132/208 |
| 5,925,615 | A | * | 7/1999 | Kern et al. .............. 510/463 |
| 2001/0007160 | A1 | * | 7/2001 | Yamaguchi et al. ....... 8/405 |
| 2002/0098230 | A1 | | 7/2002 | Nguyen et al. |
| 2005/0191263 | A1 | | 9/2005 | Ueyama et al. |
| 2005/0201966 | A1 | | 9/2005 | Ueyama et al. |
| 2005/0232893 | A1 | * | 10/2005 | Kaharu et al. .......... 424/70.27 |
| 2006/0078527 | A1 | | 4/2006 | Midha et al. |
| 2007/0071709 | A1 | * | 3/2007 | Tokunaga ............... 424/70.28 |

FOREIGN PATENT DOCUMENTS

| CN | 1679474 A | 10/2005 |
| JP | 51-26233 | 3/1976 |
| JP | 63-8319 | 1/1988 |
| JP | 63-183517 | 7/1988 |
| JP | 5-112426 | 5/1993 |
| JP | 6 279241 | 10/1994 |
| JP | 10-279444 | 10/1998 |
| JP | 11 222415 | 8/1999 |
| JP | 11-222415 | 8/1999 |
| JP | 11-335237 | 12/1999 |
| JP | 2001-97841 | 4/2001 |
| JP | 2003 501371 | 1/2003 |
| JP | 2006 160708 | 6/2006 |
| JP | 2008-515921 | 5/2008 |
| WO | WO01/76543 A1 | 10/2001 |
| WO | WO 2006/042180 A1 | 4/2006 |

OTHER PUBLICATIONS

JP 58-079913, Abstract, Retrieved on Dec. 23, 2011 on East, p. 1.*
JP06-279241, Machine Translation, retrieved online Jan. 2, 2013, 1994.*
Office Action issued Apr. 20, 2011 in Chinese Patent Application No. 200880012042.X (with English translation).
Notice of Information Statement issued on Jun. 7, 2011 in the corresponding Japanese Patent Application No. 2008-107407 (with English Translation).
Chinese Office Action mailed on Dec. 25, 2012 in corresponding Chinese Patent Application No. 200880012042.X, with English Translation, 7 pp.
Extended European Search Report issued by EPO in corresponding European Patent Application No. 08738611.6 on Jan. 8, 2015, 7 pp.

* cited by examiner

*Primary Examiner* — Brian-Yong Kwon
*Assistant Examiner* — Jennifer A Berrios
(74) *Attorney, Agent, or Firm* — Oblon, McClelland, Maier & Neustadt, L.L.P.

(57) ABSTRACT

A leave-on type hair cosmetic composition having the following two layers A and B:
  Layer A of an oil layer containing the following component (a) in an amount of 0.5-40% by mass in the hair cosmetic composition,
  (a) a highly polymerized silicone selected from dimethicone and dimethiconol and having a number average degree of polymerization of 1,000-20,000; and
  Layer B of a water layer containing the following components (b) and (c),
  (b) a water-soluble polymeric thickening agent, and
  (c) water.

16 Claims, No Drawings

HAIR COSMETIC COMPOSITION

FIELD OF THE INVENTION

The present invention relates to a leave-on type hair cosmetic composition having two or more layers.

BACKGROUND OF THE INVENTION

In recent years, it has been said that owing to the influence of chemical treatment such as hair coloring or physical treatment by blow drying, cuticles on the hair surface peel off or the hair becomes porous by the efflux of lipids from the inside of the hair and as a result, the hair inevitably becomes excessively dry, resistant to finger combing (i.e., easily entangled), untidy and lusterless.

Existing leave-on type hair cosmetic compositions which have been used for providing the hair with smoothness, luster, tidiness, and protecting the hair from excessive drying are, emulsion type products such as hair cream wax containing silicones, wax, higher alcohols, and surfactant, etc. In addition, in order to further improve the effect of providing the hair with smoothness, luster, and tidiness, it has been also known that highly polymerized silicones can be contained in a hair cosmetic composition (see, for example, Patent Document No. 1). However, because the highly polymerized silicones are difficult to be emulsified, it is usually present in an oil type composition such as hair oil that does not contain water. Such composition tends to have a sticky and unfresh feeling and has bad spreadability on the hair. As a result, it cannot easily spread over the whole hair and is not desirable in terms of tidiness of the hair. Meanwhile, in the case of an emulsion type system in which a surfactant is used with water, it is difficult to include the highly polymerized silicones in a sufficient amount, resulting in a problem in tidiness of the hair.

Meanwhile, to achieve the incorporation of liquid oil in a high concentration at an ordinary temperature, a two-layer type formulation with a water layer containing a cationic surfactant or a cationized cellulose and a soluble electrolyte and an oil layer containing a hydrophobic liquid oil has been suggested (for example, see Patent Document No. 2 and Patent Document No. 3). However, such a hair cosmetic composition cannot provide a good finish due to the sticky nature of the oil formulation.

Patent Document No. 1: JP-A-63-183517
Patent Document No. 2: JP-A-63-8319
Patent Document No. 3: JP-A-11-222415

SUMMARY OF THE INVENTION

The present invention is to provide a leave-on type hair cosmetic composition having the following two layers A and B:

Layer A of an oil layer containing the following component (a) in an amount of 0.5-40% by mass in the hair cosmetic composition,
(a) a highly polymerized silicone selected from dimethicone and dimethiconol and having a number average degree of polymerization of 1,000-20,000; and
Layer B of a water layer containing the following components (b) and (c),
(b) a water-soluble polymeric thickening agent, and
(c) water.

The leave-on type hair cosmetic composition can be applied to hair to provide a stickiness-free finish feel, smoothness, luster and tidiness.

MODE FOR CARRYING OUT THE INVENTION

The present invention relates to a hair cosmetic composition which may contain a sufficient amount of an oil layer, has no sticky feeling of an oil formulation, can be easily mixed at the time of use and applied homogeneously to hair, and can provide the hair with a stickiness-free finish feel, smoothness, luster and tidiness.

Inventors of the present invention found that by providing a leave-on hair cosmetic composition having two or more layers of an oil layer containing a highly polymerized silicone at a high concentration and a water layer containing a water-soluble polymeric thickening agent, the above-described technical problems can be solved.

<Layer A (Oil Layer)>
(a) Highly Polymerized Silicones

Layer A contains component (a), i.e., highly polymerized silicones. The highly polymerized silicones are selected from dimethicone (dimethylpolysiloxane) and dimethiconol (dimethylpolysiloxane having a hydroxy terminal group).

A number average degree of polymerization of the highly polymerized silicones is 1,000-20,000. Preferably, it is 2,000-15,000. The content of the highly polymerized silicones in the hair cosmetic composition of the present invention is, in terms of easy spreadability on hair, smoothness, and tidiness of the hair, 0.5-40% by mass. But it is preferably 2-30% by mass, more preferably 3-20% by mass, even more preferably 4-15% by mass, and even more preferably 5-10% by mass. In addition, the content of the highly polymerized silicones in layer A is preferably 3-80% by mass, more preferably 5-65% by mass, and even more preferably 9-50% by mass in view of the same aspects.

Specific examples of the commercially available highly polymerized silicones include SH200-1,000,000cs (Dow Corning Toray Co., Ltd.; highly polymerized dimethicone), TSF451-100MA (Momentive Performance Materials Inc.; highly polymerized dimethicone), BY11-026 (Dow Corning Toray Co., Ltd.; highly polymerized dimethicone solution which is diluted with a low viscosity silicone), KF9008 (Shin-Etsu Chemical Co. Ltd.; highly polymerized dimethicone solution which is diluted with a cyclic silicone), BY22-050A (Dow Corning Toray Co., Ltd.; an anionic emulsion of highly polymerized dimethicone), BY22-060 (Dow Corning Toray Co., Ltd.; a cationic emulsion of highly polymerized dimethicone solution which is diluted with a low viscosity silicone), BY22-020 (Dow Corning Toray Co., Ltd.; a cationic emulsion of highly polymerized dimethicone solution which is diluted with a light liquid isoparaffin), KM904 (Shin-Etsu Chemical Co. Ltd.; a cationic emulsion of highly polymerized dimethicone solution which is diluted with a low viscosity silicone), DC1501 Fluid (Dow Corning Toray Co., Ltd.; highly polymerized dimethiconol solution which is diluted with a cyclic silicone), DC1503 Fluid (Dow Corning Toray Co., Ltd.; highly polymerized dimethiconol solution which is diluted with a low viscosity dimethicone), X-21-5849 (Shin-Etsu Chemical Co. Ltd.; highly polymerized dimethiconol), X-21-5666 (Shin-Etsu Chemical Co. Ltd.; highly polymerized dimethiconol solution which is diluted with a cyclic silicone) and X-21-5613 (Shin-Etsu Chemical Co. Ltd.; highly polymerized dimethiconol solution which is diluted with a low viscosity dimethicone).

(d) Volatile Oils

In layer A, volatile oils of component (d) are preferably contained as a solubilizing agent for the above-described component (a). By adding the volatile oils, it becomes easy for highly polymerized silicones to form a film on the surface of the hair, and with moist and smooth finish feel, hair tidiness becomes improved. As the volatile oils, volatile silicones and hydrocarbons can be mentioned. Of these, low boiling point chain silicone oils, low boiling point cyclic silicone oils, and low boiling point isoparaffin hydrocarbons, etc. can be preferably used. In this case, low boiling point means that the boiling point is 300° C. or less, preferably 280° C. or less, and more preferably 260° C. or less at atmospheric pressure.

The low boiling point chain silicone oils are represented by the following general formula, and the specific examples include hexamethyldisiloxane, octamethyltrisiloxane, decamethyltetrasiloxane, dodecamethylpentasiloxane, tetradecamethylhexasiloxane, hexadecamethylheptasiloxane, and commercial products such as KF-96A-1.5cs, and KF-96L-2cs (Shin-Etsu Chemical Co. Ltd.).

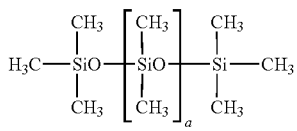

wherein a represents an integer of from 0 to 5.

The cyclic silicone oils are represented by the following general formula, and the specific examples include hexamethylcyclotrisiloxane, octamethylcyclotetrasiloxane, decamethylcyclopentasiloxane, dodecamethylcyclohexasiloxane, tetradecamethylcycloheptasiloxane, and commercial products such as KF994, and KF995 (Shin-Etsu Chemical Co. Ltd.).

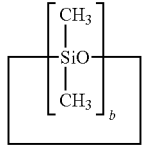

wherein b represents an integer of from 3 to 7.

The low boiling point isoparaffin hydrocarbons include light liquid isoparaffins with a boiling point of 260° C. or less at atmospheric pressure, purified products of isododecane, and a mixture of an aliphatic hydrocarbon having various chain length. Commercially available products include, IP solvent (Idemitsu Sekiyu Kagaku K.K. (currently Idemitsu Kosan, Co., Ltd., after the merge)) and Marukasol (manufactured by the same company) and the like.

Of these, in order to obtain clean senses of use and after-styling feel without any stickiness, volatile silicones are preferred, with cyclic silicones being more preferred. Of these, decamethylcyclopentasiloxane and dodecamethylcyclohexasiloxane are preferably used considering that they can be relatively stably maintained in an air-tight container. Moreover, in order to obtain moist senses of use or after-styling feel, volatile hydrocarbons are preferred, with low boiling point isoparaffinic hydrocarbons being more preferred. Of these, light liquid isoparaffins are preferred, with isododecane being more preferred. These volatile oils facilitate the drying of a water-soluble hair cosmetic composition and due to the vaporization of the oils a strong cosmetic film made of highly polymerized silicones can be formed on the hair.

Volatile oils as component (d) can be used alone or in a combination of two or more. The total content is preferably 5-69.5% by mass, more preferably 20-60% by mass, and even more preferably 30-50% by mass in the hair cosmetic composition of the present invention. In addition, the mass ratio between component (a) and component (d) is preferably 1:30-3:1, more preferably 1:20-2:1, and even more preferably 1:10-1:1 in terms of optimization between mixing and separation of layer A and layer B, easy spreadability of the composition on the hair, smoothness and excellent tidiness of the hair. In addition to the above-described components, lower alcohols such as ethanol and isopropyl alcohol and the like can be added.

Other Silicones

For layer A, in order to enhance a conditioning effect of the composition of the present invention, additional silicones other than components (a) and (d) can be further contained (e.g., other kinds of dimethicone or dimethiconol, phenylpolysiloxane, amino modified silicones and polyether modified silicones, etc).

Oil Component

For layer A, in order to enhance the tidy feeling of the hair after dry, an oil component can be contained. Examples of the oil component include hydrocarbons such as squalene, squalane, liquid isoparaffin, heavy liquid isoparaffin, α-olefin oligomer, liquid paraffin, and cycloparaffin; glycerides such as castor oil, cacao oil, mink oil, avocado oil, and olive oil; waxes such as bees wax, sperm wax, lanolin, micro crystalline wax, ceresin wax, and carnauba wax; higher alcohols such as cetyl alcohol, oleyl alcohol, stearyl alcohol, isostearyl alcohol, and 2-octyldodecanol; esters such as octyl dodecyl myristate, hexyl laurate, cetyl lactate, propylene glycol monostearate, oleyl oleate, hexadecyl 2-ethylhexanoic acid, isononyl isononanoic acid, tridecyl isononanoic acid, and isopropyl palmitate; higher fatty acids such as capric acid, lauric acid, myristic acid, palmitic acid, stearic acid, behenic acid, oleic acid, palm oil fatty acid, isostearic acid, and isopalmitic acid and; isostearylglyceryl ether and polyoxypropylenebutyl ether. Of these, branched hydrocarbons such as squalene, squalane, liquid isoparaffin, heavy liquid isoparaffin, and α-olefin oligomer are preferred.

Preferably, the content of the oil component in the hair cosmetic composition of the present invention is, in terms of excellent tidiness and stickiness-free feel of the hair, 0.1-15% by mass. But it is more preferably 0.5-12% by mass, and even more preferably 1-10% by mass.

Water

Layer A is preferably transparent. In addition, to ensure a complete separation from layer B, the content of water in layer A is preferably 5% by mass or less, more preferably 3% by mass or less, and even more preferably 1% by mass or less in the hair cosmetic composition of the present invention. Water content in layer A is measured according to the Karl Fisher method as described in JIS K 0068, after it is stirred at 25° C. and kept at the same temperature for 48 hours, and then only layer A is taken for the measurement by using a syringe, etc. In the present invention, a titrator manufactured by Hiranuma Sangyo Corporation (Model No. AQV-7) was used as a detector for measuring water content while methanol-chloroform was used as a solvent. In this case, after adjusting the mass ratio of methanol-chloroform to 1:3, the hair cosmetic composition that is to be tested is dissolved in the solvent mixture. If the composition is insoluble in the solvent mixture, the ratio between methanol and chloroform is changed to 2:1. If the composition still remains insoluble, 100% methanol is used as a solvent.

<Layer B (Water Layer)>

Layer B contains a water-soluble polymeric thickening agent and water as component (b) and (c), respectively.

(b) Water-Soluble Polymeric Thickening Agent

As a water-soluble polymeric thickening agent of component (b), polysaccharides, acrylic polymer compound, carboxyvinyl polymer, polyvinyl alcohol, polyvinylpyrrolidone and derivatives thereof can be mentioned. Of these, polysaccharides, acrylic polymer compound, and derivatives thereof are preferred.

Examples of the polysaccharides include cellulose, guar gum, cellulose gum, and starch. The derivatives of the polysaccharides are preferably those substituted with at least one substituent that is described below.

Examples of the substituent includes a lower alkyl group such as a methyl group, an ethyl group, and a propyl group, which may be substituted with a hydroxy group; a lower alkyl group such as a methyl group, an ethyl group, and a propyl group, which may be substituted with a carboxy group; a linear or branched alkyl group, an alkenyl group, an arylalkyl group, an alkylaryl group, an alkoxy group, an alkoxyalkyl group, an alkenyloxy group, an alkenyloxyalkyl group, an arylalkyloxy group, an arylalkyloxyalkyl group, an alkylaryloxy group, an alkylaryloxyalkyl group, which have a total carbon number of 8-40 and may be substituted with a hydroxy group; an alkylglycerylether group having a linear or branched alkyl group with a carbon number of 10-40, an alkenylglycerylether group having a linear or branched alkenyl group with a carbon number of 10-40; a polyoxyethylene group, a polyglycerin group, a sulfoalkyl group, a trimethylammonium group, and a trimentylammoniumalkyl group. In case the substituent has a hydroxy group, the hydroxy group can be also substituted with a different substituent described above.

Specific examples of the derivatives of the polysaccharide include hydroxyethyl cellulose, hydroxyethyl guar gum, hydroxyethyl starch, methyl cellulose, methyl guar gum, methyl starch, ethyl cellulose, ethyl guar gum, ethyl starch, hydroxypropyl cellulose, hydroxypropyl guar gum, hydroxypropyl starch, hydroxyethylmethyl cellulose, hydroxyethylmethyl guar gum, hydroxyethylmethyl starch, hydroxypropylmethyl cellulose, stearoxy PG hydroxyethyl cellulose sodium sulfonate, laureth-13PG hydroxyethyl cellulose, stearoxy PG hydroxyethyl cellulose, cationized hydroxyethyl cellulose(polyquaternium-10), hydroxypropylmethyl guar gum, hydroxypropylmethyl starch, carboxymethyl cellulose, and carboxymethyl cellulose sodium.

Specific examples of the acrylic polymer compound or derivative thereof include polyacrylic acid, polymethacrylic acid, acrylic acid-methacrylic acid copolymer, acrylic acid-methacrylic acid alkyl copolymer, acrylic acid alkyl copolymer, polyacrylic acid, sodium polyacrylic acid, polyacrylic amide, cationized methacrylic diethyl sulfonate•cationized acrylic amide•dimethacrylic acid polyethylene glycol copolymer (polyquaternium-52), and cationized methacryloylethyl polymer (polyquaternium-37).

Of these, stearoxy PG hydroxyethyl cellulose sodium sulfonate, cationized methacrylic diethyl sulfonate•cationized acrylic amide•dimethacrylic acid polyethylene glycol copolymer (polyquaternium-52), cationized methacryloylethyl polymer (polyquaternium-37), and hydroxyethyl cellulose, etc. are preferred.

The content of the water-soluble polymeric thickening agent as component (b) is, to ensure a good state of mixing right after the mixing and a good state of separation after leaving the composition for some time, preferably 0.005-5% by mass, more preferably 0.01-2% by mass, and even more preferably 0.05-1% by mass in the hair cosmetic composition of the present invention.

(C) Water

The content of water as component (c) is preferably 10-80% by mass, more preferably 20-60% by mass, and even more preferably 30-50% by mass in the hair cosmetic composition of the present invention.

(e) Organic Solvent

It is preferable that layer B further contains an organic solvent as component (e) which is selected from a group consisting of aromatic alcohols, N-alkyl pyrrolidone, alkylene carbonate, polypropylene glycol, lactones and cyclic ketones and has a ClogP value of from −2 to 3.

As the organic solvent of component (e), compounds that are represented by the following (e1)-(e5) can be mentioned.

(e1) Aromatic alcohols represented by general formula (1):

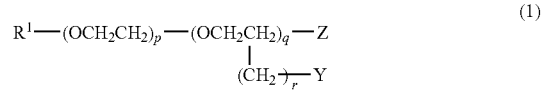

wherein $R^1$ represents a group $R^2$-Ph-$R^3$— ($R^2$; a hydrogen atom, a methyl group or a methoxy group, $R^3$; a bond or a saturated or unsaturated divalent hydrocarbon group of carbon number 1 to 3, Ph; paraphenylene group), Y and Z each represents a hydrogen atom or a hydroxy group, and p, q and r each stands for an integer of from 0 to 5, with the proviso that when $p=q=0$, Z does not represent a hydrogen atom and $R^1$ does not represent a group $R^2$-Ph-.

(e2) N-alkylpyrrolidone having a nitrogen atom to which an alkyl group of carbon number 1 to 18 is bonded.

(e3) alkylene carbonate of carbon number 3 to 4.

(e4) Polypropylene glycols having a number average molecular weight of from 100 to 1000.

(e5) Lactones or cyclic ketones represented by any one of the general formulae (2), (3) or (4).

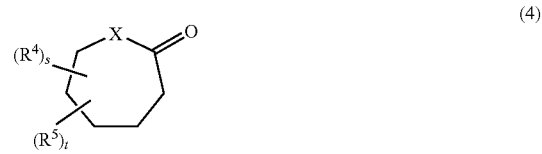

wherein X represents a methylene group or an oxygen atom, $R^4$ and $R^5$ respectively represent substituents which are different from each other, and s and t each stands for 0 or 1.

Of the organic solvents serving as component (e), examples of (e1) include benzyl alcohol, cinnamyl alcohol, phenethyl alcohol, p-anisyl alcohol, p-methylbenzyl alcohol, phenoxyethanol, and 2-benzyloxyethanol; those of (e2) include N-methylpyrrolidone, N-octylpyrrolidone and N-laurylpyrrolidone; and those of (e3) include ethylene carbonate and propylene carbonate. As the polypropylene glycol (e4) having a number average molecular weight of from 100 to 1000, those having a number average molecular weight of from 100 to 500 are preferred, and those having a degree of polymerization of from 2 to 5 are more preferred. In (e5), $R^4$ and $R^5$ in the formulae (2) to (4) are each preferably a linear, branched or cyclic alkyl group, hydroxy group, sulfonic acid group, phosphoric acid group, carboxy group, phenyl group, sulfoalkyl group, phosphoric acid alkyl group and carboxyalkyl group. Of these, linear or branched alkyl groups of carbon number 1 to 6 such as methyl group, ethyl group, propyl group, isopropyl group and butyl group substituted at the γ position in the case of γ-lactone and substituted at the δ position (i.e., methylene adjacent to the hetero oxygen atom) in the case of δ-lactone are preferred. In order to enhance the water solubility of the compounds (2) to (4), $R^4$ or $R^5$ preferably represents an acid group such as sulfonic acid group, phosphoric acid group or carboxy group, or an alkyl group substituted therewith. In (e5), examples of the lactones include γ-butyrolactone, γ-caprolactone, γ-valerolactone, δ-valerolactone, δ-caprolactone and δ-heptanolactone. Of these, γ-lactone is preferred, with γ-butyrolactone and γ-caprolactone being more preferred in terms of the stability of the lactones. Examples of the cyclic ketones as (e5) include cyclopentanone, cyclohexanone, cycloheptanone and 4-methylcycloheptanone.

Examples of the preferred component (e) include benzyl alcohol, 2-benzyloxyethanol, propylene carbonate and polypropylene glycol (number average molecular weight of from 300 to 500, preferably 400).

Component (e) to be used in the present invention is preferably a liquid at 25° C. and has a ClogP of from −2 to 3, preferably from −1 to 2 in view of penetration promotion. The term "ClogP" as used herein means a measure indicating the distribution of a substance between an octanol phase and an aqueous phase and it is a calculated value of an octanol-water distribution coefficient (logP) as defined by the below-described equation and its examples are described in Chemical Reviews, 71(6), 1971.

$$\log P = \log([\text{Substance}]_{Octanol}/[\text{Substance}]_{Water})$$

wherein $[\text{Substance}]_{Octanol}$ means a mole concentration of a substance in a 1-octanol phase, while $[\text{Substance}]_{Water}$ means a mole concentration of the substance in an aqueous phase.

The ClogP of each of the main compounds usable as component (e) is as follows: benzyl alcohol (1.1), 2-benzyloxyethanol (1.2), 2-phenylethanol (1.2), 1-phenoxy-2-propanol (1.1), polypropylene glycol 400 (0.9), propylene carbonate (−0.41), and γ-butyrolactone (−0.64).

As component (e), two or more compounds may be used in combination. Their content in the hair cosmetic composition of the present invention is preferably from 0.05 to 10% by mass, more preferably from 0.1 to 5% by mass, even more preferably from 0.5 to 4% by mass, and even more preferably from 1 to 3% by mass, in view of the optimization between mixing and separation of layer A and layer B, senses of use, and promotion of hair quality and luster improving effects (improvement of elasticity, improvement of moisture resistance, and the like).

(f) Organic Carboxylic Acid or Salts Thereof

It is preferred that layer B further contains an organic carboxylic acid of carbon number 2 to 8 or salts thereof as component (f). As the organic carboxylic acid of carbon number 2 to 8, glycolic acid, lactic acid, citric acid, tartaric acid, malic acid, levulinic acid, acetic acid, maleic acid, and fumaric acid and the like can be mentioned. Of these, α-hydroxy acid is preferred, and glycolic acid, citric acid, malic acid and lactic acid are more preferred with malic acid, lactic acid and citric acid being even more preferred. Examples of the salts of these organic carboxylic acids include salts with an alkali metal, alkaline earth metal, ammonia or organic amine compound. The organic acid or salts thereof can be used in a combination of two or more.

Component (f) can be used in a combination of two or more and it is preferable that at least malic acid or salts thereof is used. The content of component (f) in the hair cosmetic composition of the present invention is preferably from 0.5 to 10% by mass, more preferably from 1 to 8% by mass, and even more preferably from 2 to 6% by mass in terms of free acid amount for obtaining an effect of modifying the hair core (i.e., porosity repair, etc.), improving tidiness of the hair, enhancing holding power of hair setting, and moisture-resistant tidiness of the hair.

The mass ratio between the organic solvent of component (e) and the organic carboxylic acid or salt thereof as component (f) is preferably 1:10-7:1, more preferably 1:4-3:1 for efficiently achieving an effect of modifying the hair core (i.e., porosity repair, etc.), enhancing holding power of hair setting and improving tidiness of the hair, etc.

Ethanol

Layer B may further contain ethanol. Ethanol lowers surface tension of water layer so that the composition of the present invention can easily penetrate into the hair. It further contributes to the solubilization or stable dispersion of the organic solvent of component (e). The content of ethanol in the hair cosmetic composition of the present invention is preferably from 0.5 to 20% by mass, more preferably from 1 to 15% by mass. A mass ratio of ethanol to component (e) preferably ranges from 40:1 to 2:1, more preferably from 20:1 to 3:1 from the viewpoint of penetration promotion of components (e) and (f) into the hair.

Surfactant

In layer B, a surfactant may be incorporated from the viewpoints of stability of the system including the solubilization or dispersion of the solvent, and improvement in the feel of the hair. As the surfactant, any one of cationic surfactant, nonionic surfactant, amphoteric surfactant and anionic surfactant can be used.

Examples of the cationic surfactant include quaternary ammonium salts represented by the following general formula (5):

(5)

wherein $R^6$ and $R^7$ each independently represents a hydrogen atom, a alkyl group of carbon number 1 to 28 or a benzyl group, with the proviso that they do not simultaneously represent a hydrogen atom, a benzyl group or a lower alkyl group of carbon number 1 to 3, and $Z^-$ represents an anion.

Either one of $R^6$ and $R^7$ preferably represents an alkyl group of carbon number 16 to 24, more preferably carbon number 16 to 18, even more preferably a linear alkyl group, while the other one represents a lower alkyl group of carbon number 1 to 3, preferably a methyl group. Examples of the anion $Z^-$ include halide ions such as chloride ion and bromide ion, and organic anions such as an ethyl sulfate ion and a methyl carbonate ion. Of these, halide ions are preferred, with chloride ion being more preferred.

As the cationic surfactant, mono(long chain alkyl) quaternary ammonium salts are preferred. Specific examples include cetyltrimethylammonium chloride, stearyltrimethylammonium chloride, aralkyltrimethylammonium chloride and behenyltrimethylammonium chloride. Of these, stearyltrimethylammonium chloride and behenyltrimethylammonium chloride are preferred.

Examples of the nonionic surfactant include polyoxyalkylene alkyl ethers, polyoxyalkylene alkenyl ethers, higher fatty acid sucrose esters, polyglycerin fatty acid esters, higher fatty acid mono- or di-ethanolamides, polyoxyethylene hydrogenated castor oils, polyoxyethylene sorbitan fatty acid esters, polyoxyethylene sorbitol fatty acid esters, alkyl saccharide surfactants, alkylamine oxides, and alkyl amidoamine oxides. Of these, polyoxyalkylene alkyl ethers and polyoxyethylene hydrogenated castor oils are preferred, with polyoxyethylene alkyl ethers being more preferred.

As the amphoteric surfactant, imidazoline, carbobetaine, amidobetaine, sulfobetaine, hydroxysulfobetaine, and amidosulfobetaine surfactants, etc. can be used.

Examples of the anionic surfactant include alkylbenzene sulfonates, alkyl or alkenyl ether sulfates, alkyl or alkenyl sulfates, olefin sulfonates, alkane sulfonates, saturated or unsaturated fatty acid salts, alkyl or alkenyl ether carboxylates, $\alpha$-sulfone fatty acid salts, N-acylamino acid surfactants, mono- or di-ester type phosphate surfactants and sulfosuccinates.

Examples of the counterion to the anionic residue of the above-described surfactants include alkali metal ions such as sodium ion and potassium ion; alkaline earth metal ions such as calcium ion and magnesium ion; ammonium ion, and alkanolamines having 1 to 3 alkanol groups of carbon number 2 or 3 (such as monoethanolamine, diethanolamine, triethanolamine and triisopropanolamine).

In addition, examples of the counterion to the cationic residue of the above-described surfactants include halide ions such as chloride ion, bromide ion and iodide ion, methosulfate ion and saccharinate ion.

Of these, cationic surfactants are preferred in view of feel of the hair. These surfactants may be used either alone or in a combination of two or more. The content of the surfactant (s) in the hair cosmetic composition of the present invention is preferably from 0.01 to 5% by mass, more preferably from 0.05 to 3% by mass, and even more preferably 0.1 to 1% by mass, in view of stability of the system including solubilization of the solvent, emulsification of an oil component, and suspension stability upon mixing, etc. A mass ratio of component (e) to the surfactant preferably ranges from 500:1 to 1:10, more preferably from 100:1 to 1:5, even more preferably from 10:1 to 1:2 in view of the optimization between mixing and separation of layer A and layer B, promotion of hair smoothness, and easy spreadability of the composition to the hair.

Polyhydric Alcohol

Layer B may further contain a polyhydric alcohol. The polyhydric alcohol improves luster and the hair quality improving effect and contributes to solubilization and stable dispersion of component (e). Examples of the polyhydric alcohol include ethylene glycol, glycerin, sorbitol, propylene glycol, 1,3-butylene glycol and dipropylene glycol. Of these, glycerin, propylene glycol, 1,3-butylene glycol and dipropylene glycol are preferred. These polyhydric alcohols may be used either alone or in a combination of two or more. Their content in the hair cosmetic composition of the present invention is preferably from 0.5 to 5% by mass, more preferably from 1 to 3% by mass.

pH

In view of providing the hair with elasticity/resilience, luster improvement, softness, tidiness and suppleness, the pH of layer B is, in the case of preparing into a 20-fold dilution with water, preferably adjusted to 2 to 5.5, more preferably 2.5 to 5, and even more preferably 3 to 4.5 at 25° C. In order to adjust the pH within the range, an inorganic acid such as hydrochloric acid, sulfuric acid and phosphoric acid and an alkalinizing agent such as sodium hydroxide and potassium hydroxide and the like can be used in addition to the organic carboxylic acid contained as component (f) in the composition of the present invention.

In order to inhibit any change in pH of the composition when it is applied to the hair, to facilitate the penetration of the organic solvent as component (e) and the organic carboxylic acid as component (f) into the hair, to obtain quick expression of the hair modifying effect and to enhance the feeling of such an effect, layer B is required to have a buffer capacity not lower than 0.001 gram equivalent/L but lower than 0.2 gram equivalent/L, preferably not lower than 0.003 gram equivalent/L but lower than 0.1 gram equivalent/L, more preferably not lower than 0.005 gram equivalent/L but lower than 0.05 gram equivalent/L. The term "buffer capacity" as used herein means a value determined by the following equation while using as a measure the concentration of a base required to raise the pH of the 5% by mass aqueous solution at 25° C. by 1 from its initial value.

$$\text{Buffer capacity} = [dC_B/dpH]$$

wherein $C_B$ represents an ion concentration (gram equivalent/L) of the base.

Such a buffer capacity can be imparted by adding a pH buffering agent or the like to the hair cosmetic composition. Usable as the pH buffering agent is a combination of an organic acid or inorganic acid and a salt thereof, which has buffering action in a pH range of from 2 to 5.5. Component (f) is used as an organic acid and examples of the inorganic acid can include phosphoric acid, sulfuric acid, and nitric acid. Further, examples of the salt of such an acid can include its alkali metal salts such as sodium salts and potassium salts; its ammonium salts; and its alkanolamine salts such as triethanolamine salts. No particular limitation is imposed on the amount of the pH buffering agent to be added, and its amount varies depending on the kind of the compound giving buffer capacity. When sodium citrate is used as a primary compound giving the buffer capacity, for example, it can be added at a concentration of about 1% by mass or higher.

For layer A, a setting polymer can be further contained in addition to the components in view of improvement in hair manageability.

<Others (Common for Layer A and Layer B)>

Other Components

The hair cosmetic composition of the present invention may further contain, in addition to the above-described components, as needed, components employed for ordinary hair cosmetic compositions depending on their purpose of use. Examples of such components include anti-dandruffs; vitamin preparations; bactericides; anti-inflammatories; preservatives; chelating agents; humectants such as panthenol; coloring agents such as dyes and pigments; plant extracts; pearlescent agents; perfumes; ultraviolet absorbers; antioxidants; and the other components as described in the ENCYCLOPEDIA OF SHAMPOO INGREDIENTS (MICELLE PRESS).

Ratio Between Layer A and Layer B

The mass ratio between layer A and layer B of the hair cosmetic composition of the invention ranges from 15:85 to 70:30, more preferably from 30:70 to 60:40 in view of providing the hair with smoothness, luster, tidiness and compatibility with hair modification and an easiness for mixing.

The hair cosmetic composition of the present invention can be provided as, in addition to a two-layer type with layer A and layer B, a three or more-layer type which further contains an oil layer, an emulsifying layer, or a powder layer that are not soluble in layer A or layer B. Moreover, the hair cosmetic composition of the present invention is preferably used in a form of a hair styling agent or a leave-on hair conditioning agent and the like.

Since the effect of the hair cosmetic composition of the present invention is most prominent right after the mixing of the components, in order to make the time point of showing such high effect clear, it is preferable that either one of layer A and layer B is colored or both layers are colored with a different color and the hair cosmetic composition is filled in a transparent or a semi-transparent container. By doing so, the degree of mixing can be visually determined so that the effect of the hair cosmetic composition of the present invention can be more conveniently obtained.

Dyestuff is used for coloring. An acidic dye or a basic dye can be preferably used. The acidic dye is more preferable. More specifically, examples of the acidic dye include Blue No. 1, Purple No. 401, Black No. 401, Orange No. 205, Red No. 227, Red No. 106, Yellow No. 203, and Acid Orange No. 3. Examples of the basic dye include Basic Blue No. 99, Basic Brown No. 16, Basic Brown No. 17, Basic Red No. 76, Basic Red No. 51, Basic Yellow No. 57, Basic Yellow No. 87 and Basic Orange No. 31.

<Method of Use>

Meanwhile, the hair cosmetic composition of the present invention is first shaken well before use, dispensed to the hands before it starts getting separated into layer A and layer B, and spread well on the palm and then applied to the hair. By heating after application of the hair cosmetic composition of the present invention to the hair or by natural drying thereof, formation of a film of component (a) on the hair and penetration of components (e) and (f) into the hair can be accelerated. Heating is more preferable. For heating, a drier, a heater or a hair curler and the like can be used. The heating temperature is preferably 50° C. or greater, more preferably 70° C. or greater.

EXAMPLES

In the following Examples, each "pH" indicates a pH as measured when diluted 20-fold by mass with water at 25° C.

Examples 1-11 and Comparative Examples 1-3

Hair cosmetic compositions were prepared as described in Table 1 and Table 2. Then, they were evaluated in terms of "easy applicability (hardly dripping from the hands) (easily spread on the hair)", "tidiness", "smoothness", and "duration of maintaining a mixing state". Results are together shown below.

<Preparation Method>

Layer A and layer B described in Table 1 and Table 2 are mixed separately and then filled into a bottle (Examples 1-12 and Comparative Examples 1 and 2). Meanwhile, Comparative Example 3 consists of layer A only.

<Evaluation Method•Evaluation Criteria>

Easy applicability to the hair (hardly dripping from the hands, easily spread on the hair), tidiness and smoothness of the hair right after the application Professional panelists evaluated the hair cosmetic compositions in accordance with the following four-level criteria.

A: Very good, B: Good, C: Slightly bad, D: Bad

Duration of Maintaining a Mixing State

A bottle containing each hair cosmetic composition was shaken at 25° C. until a homogeneous mixture was formed. The bottle was then kept at the same temperature. The mixing state after five minutes and the separation state after 60 minutes and 8 hours, respectively, were observed and evaluated according to the criteria described below. Right after the mixing, it is preferable that the mixing state is maintained for a time that is sufficient for applying the composition to the hair. After that state, however, it is preferable that the composition is separated into the original state.

Mixing state, 5 minutes after the mixing

A: A homogeneous mixing state is maintained, B: A little separation occurs, C: Separation occurs.

Separation state, 60 minutes and 8 hours, respectively, after the mixing

A: Clean separation into the original state (two layers), B: In a partial mixing state, C: In a mixing state.

TABLE 1

| Component (% by mass) | Example | | | | | | |
|---|---|---|---|---|---|---|---|
| | 1 | 2 | 3 | 4 | 5 | 6 | 7 |
| Oil layer (layer A) | | | | | | | |
| (a) Dimethylpolysiloxane (n = 2600) | 6.00 | 6.00 | 6.00 | 6.00 | 6.00 | 6.00 | 6.00 |
| Dimethylpolysiloxane (10 mPa · s) | — | — | — | — | — | — | — |
| (d) Isododecane | 32.90 | — | — | 32.90 | 32.90 | 32.90 | 69.90 |
| (d) Cyclopentasiloxane | — | 32.90 | — | — | — | — | — |
| (d) Liquid isoparaffin | — | — | 32.90 | — | — | — | — |
| Dicapric acid neopentyl glycol | 6.00 | 6.00 | 6.00 | 6.00 | 6.00 | 6.00 | 6.00 |
| Fragrances | 0.10 | 0.10 | 0.10 | 0.10 | 0.10 | 0.10 | 0.10 |
| Oil layer (layer A) Total | 45 | 45 | 45 | 45 | 45 | 45 | 45 |
| Water layer (layer B) | | | | | | | |
| (b) Stearoxy PG hydroxyethyl cellulose sodium sulfonate (*1) | 0.10 | 0.10 | 0.10 | — | — | — | — |
| (b) Sodium Carboxymethyl cellulose (*2) | — | — | — | 0.10 | — | — | — |
| (b) Polyquaternium-37 (*3) | — | — | — | — | 0.10 | — | — |
| (b) Aqueous solution of polyquaternium-52 (*4) | — | — | — | — | — | 2.50 | — |
| (b) Hydroxyethyl cellulose | — | — | — | — | — | — | 0.10 |
| Yellow No. 203 | 0.0013 | 0.0013 | 0.0013 | 0.0013 | 0.0013 | 0.0013 | 0.0013 |
| (f) Aqueous solution of malic acid (50%) | 2.50 | 2.50 | 2.50 | 2.50 | 2.50 | 2.50 | 2.50 |
| (f) Lactic acid (90%) | 3.60 | 3.60 | 3.60 | 3.60 | 3.60 | 3.60 | 3.60 |
| (e) Benzyl alcohol | 1.40 | 1.40 | 1.40 | 1.40 | 1.40 | 1.40 | 1.40 |

TABLE 1-continued

| Component (% by mass) | Example 1 | 2 | 3 | 4 | 5 | 6 | 7 |
|---|---|---|---|---|---|---|---|
| Aqueous solution of stearyltrimethylammonium chloride (*5) | 0.90 | 0.90 | 0.90 | 0.90 | 0.90 | 0.90 | 0.90 |
| Trideceth-9 (*6) | 0.30 | 0.30 | 0.30 | 0.30 | 0.30 | 0.30 | 0.30 |
| PEG-7 glycerylcocoate | 1.00 | 1.00 | 1.00 | 1.00 | 1.00 | 1.00 | 1.00 |
| Glycerin | 2.50 | 2.50 | 2.50 | 2.50 | 2.50 | 2.50 | 2.50 |
| Ethanol | 8.00 | 8.00 | 8.00 | 8.00 | 8.00 | 8.00 | 8.00 |
| (e) Phenoxyethanol | 0.35 | 0.35 | 0.35 | 0.35 | 0.35 | 0.35 | 0.35 |
| Oxybenzone-9 | 0.05 | 0.05 | 0.05 | 0.05 | 0.05 | 0.05 | 0.05 |
| Sodium hydroxide | (*7) | (*7) | (*7) | (*7) | (*7) | (*7) | (*7) |
| (c) Water | Balance | Balance | Balance | Balance | Balance | Balance | Balance |
| Water layer (layer B) Total | 55 | 55 | 55 | 55 | 55 | 55 | 55 |
| Evaluation Easiness of application | | | | | | | |
| Hardly dripping from hands | A | A | A | C | B | B | A |
| Easily spread on the hair | A | A | A | A | A | A | C |
| Tidiness | A | A | B | B | B | B | B |
| Smoothness | A | A | C | A | A | A | C |
| Mixing state, 5 minutes after the mixing | A | A | A | B | B | B | A |
| Separation state, 60 minutes after the mixing | A | A | A | A | A | A | B |
| Separation state, 8 hours after the mixing | A | A | A | A | A | A | A |

TABLE 2

| Component (% by mass) | Example 8 | 9 | 10 | 11 | Comparative Example 1 | 2 | 3 |
|---|---|---|---|---|---|---|---|
| Oil layer (layer A) | | | | | | | |
| (a) Dimethylpolysiloxane (n = 2600) | 6.00 | 6.00 | 6.00 | 6.00 | — | 6.00 | 30.00 |
| Dimethylpolysiloxane (10 mPa · s) | — | — | — | — | 6.00 | — | — |
| (d) Isododecane | 32.90 | 32.90 | 32.90 | 32.90 | 32.90 | 32.90 | 69.90 |
| (d) Cyclopentasiloxane | — | — | — | — | — | — | — |
| (d) Liquid isoparaffin | — | — | — | — | — | — | — |
| Dicapric acid neopentyl glycol | 6.00 | 6.00 | 6.00 | 6.00 | 6.00 | 6.00 | — |
| Fragrances | 0.10 | 0.10 | 0.10 | 0.10 | 0.10 | 0.10 | 0.10 |
| Oil layer (layer A) Total | 45 | 45 | 45 | 45 | 45 | 45 | 100 |
| Water layer (layer B) | | | | | | | |
| (b) Stearoxy PG hydroxyethyl cellulose sodium sulfonate (*1) | 0.10 | — | — | — | 0.10 | — | — |
| (b) Sodium carboxymethyl cellulose (*2) | — | — | — | — | — | — | — |
| (b) Polyquaternium-37 (*3) | — | 0.10 | — | — | — | — | — |
| (b) Aqueous solution of polyquaternium-52 (*4) | — | — | 2.50 | — | — | — | — |
| (b) Hydroxyethyl cellulose | — | — | — | 0.10 | — | — | — |
| Yellow No. 203 | 0.0013 | 0.0013 | 0.0013 | 0.0013 | 0.0013 | 0.0013 | — |
| (f) Aqueous solution of malic acid (50%) | — | — | — | — | 2.50 | 2.50 | — |
| (f) Lactic acid (90%) | — | — | — | — | 3.60 | 3.60 | — |
| (e) Benzyl alcohol | 1.40 | 1.40 | 1.40 | 1.40 | 1.40 | 1.40 | — |
| Aqueous solution of stearyltrimethylammonium chloride (*5) | 0.90 | 0.90 | 0.90 | 0.90 | 0.90 | 0.90 | — |
| Trideceth-9 (*6) | — | — | — | — | 0.30 | 0.30 | — |
| PEG-7 glycerylcocoate | 1.00 | 1.00 | 1.00 | 1.00 | 1.00 | 1.00 | — |
| Glycerin | 2.50 | 2.50 | 2.50 | 2.50 | 2.50 | 2.50 | — |
| Ethanol | 8.00 | 8.00 | 8.00 | 8.00 | 8.00 | 8.00 | — |
| (e) Phenoxyethanol | 0.35 | 0.35 | 0.35 | 0.35 | 0.35 | 0.35 | — |
| Oxybenzone-9 | 0.05 | 0.05 | 0.05 | 0.05 | 0.05 | 0.05 | — |
| Sodium hydroxide | — | — | — | — | (*7) | (*7) | — |
| (c) Water | Balance | Balance | Balance | Balance | Balance | Balance | — |
| Water layer (layer B) Total | 55 | 55 | 55 | 55 | 55 | 55 | — |
| Evaluation Easiness of application | | | | | | | |
| Hardly dripping from hands | A | A | B | A | C | D | A |
| Easily spread on the hair | B | A | A | C | A | B | D |
| Tidiness | B | B | B | B | C | B | C |

TABLE 2-continued

|  | Example | | | | Comparative Example | | |
| --- | --- | --- | --- | --- | --- | --- | --- |
| Component (% by mass) | 8 | 9 | 10 | 11 | 1 | 2 | 3 |
| Smoothness | A | A | A | C | D | C | D |
| Mixing state, 5 minutes after the mixing | A | A | A | A | C | C | — |
| Separation state, 60 minutes after the mixing | B | B | B | B | A | A | — |
| Separation state, 8 hours after the mixing | B | B | B | A | A | A | — |

(*1) KAO CORPORATION SPS-S-SA
(*2) DAICEL CHEMICAL INDUSTRIES, LTD. CMC DAICEL 1350
(*3) 3V SIGMA SYNTHALEN CR
(*4) KAO CORPORATION SOFCARE KG-301W (act 4%)
(*5) KAO CORPORATION QUARTAMIN 86W
(*6) NIPPON SHOKUBAT CO., LTD. SOFTANOL 90
(*7) an amount to achieve pH 3.7.

The invention claimed is:

1. A leave-on type hair cosmetic composition comprising layers A and B:
   Layer A: an oil layer comprising component (a) in an amount of 4-40% by mass in the hair cosmetic composition,
   (a) a highly polymerized silicone selected from the group consisting of dimethicone and dimethiconol and having a number average degree of polymerization of 1,000-2,600, and
   (d) a volatile silicone oil or a volatile hydrocarbon,
   wherein the mass ratio of component (a) to component (d) ranges from 1:10 to 1:1; and
   Layer B: a water layer comprising components (b) and (c),
   (b) a water-soluble polymeric thickening agent selected from the group consisting of a polysaccharide a derivative of a polysaccharide, and
   (c) water;
   wherein the water-soluble polymeric thickening agent does not comprise a cationized hydroxyethyl cellulose.

2. The hair cosmetic composition according to claim 1, wherein the content of component (a) in layer A is 3-80% by mass.

3. The hair cosmetic composition according to claim 1, wherein layer B further comprises component (e):
   (e) an organic solvent which is selected from the group consisting of an aromatic alcohol, N-alkyl pyrrolidone, an alkylene carbonate, a polypropylene glycol, a lactone and a cyclic ketone and has a ClogP value of from −2 to 3.

4. The hair cosmetic composition according to claim 1, wherein layer B further comprises component (f) and the pH is from 2 to 5.5 at 25° C. when the composition is prepared into a 20-fold dilution with water:
   (f) an organic carboxylic acid of carbon number 2 to 8 or a salt thereof.

5. The hair cosmetic composition according to claim 1, wherein the content of the volatile oil in the hair cosmetic composition is 5-69.5% by mass.

6. The hair cosmetic composition according to claim 1, wherein Layer A further comprises water in an amount of 5% by mass or less.

7. The hair cosmetic composition according to claim 1, wherein the water-soluble polymeric thickening agent is a polysaccharide.

8. The hair cosmetic composition according to claim 7, wherein said polysaccharide is selected from the group consisting of cellulose, guar gum, cellulose gum, and starch.

9. The hair cosmetic composition according to claim 1, wherein the water-soluble polymeric thickening agent is a derivative of a polysaccharide.

10. The hair cosmetic composition according to claim 9, wherein said polysaccharide is selected from the group consisting of hydroxyethyl cellulose, hydroxyethyl guar gum, hydroxyethyl starch, methyl cellulose, methyl guar gum, methyl starch, ethyl cellulose, ethyl guar gum, ethyl starch, hydroxypropyl cellulose, hydroxypropyl guar gum, hydroxypropyl starch, hydroxyethylmethyl cellulose, hydroxyethylmethyl guar gum, hydroxyethylmethyl starch, hydroxypropylmethyl cellulose, stearoxy PG hydroxyethyl cellulose sodium sulfonate, laureth-13PG hydroxyethyl cellulose, stearoxy PG hydroxyethyl cellulose, hydroxypropylmethyl guar gum, hydroxypropylmethyl starch, carboxymethyl cellulose, and carboxymethyl cellulose sodium.

11. The hair cosmetic composition according to claim 1, wherein the content of the water-soluble polymeric thickening agent ranges from 0.005-5% by mass in the hair cosmetic composition.

12. The hair cosmetic composition according to claim 1, wherein the content of water ranges from 10-80% by mass in the hair cosmetic composition.

13. The hair cosmetic composition according to claim 1, wherein the content of component (a) in layer A is 5 to 65% by mass.

14. The hair cosmetic composition according to claim 1, wherein the content of component (a) in layer A is 4-15% by mass and the content of component (d) in layer A is 20-69.5% by mass.

15. The hair cosmetic composition according to claim 1, wherein the content of component (b) in layer B is 0.05-1% by mass.

16. The hair cosmetic composition according to claim 1, wherein the mass ratio between layer A and layer B is from 30:70 to 70:30.

* * * * *